United States Patent
Mak et al.

(10) Patent No.: US 9,671,280 B2
(45) Date of Patent: Jun. 6, 2017

(54) LED TESTING PROCESS AND CORRECTION METHODS THEREFOR

(71) Applicants: Ka Yee Mak, Kwai Chung (HK); Sai Kit Wong, Kwai Chung (HK); Xiao Lan Liu, Chengdu (CN); Jian Jun Ju, Chengdu (CN)

(72) Inventors: Ka Yee Mak, Kwai Chung (HK); Sai Kit Wong, Kwai Chung (HK); Xiao Lan Liu, Chengdu (CN); Jian Jun Ju, Chengdu (CN)

(73) Assignee: ASM TECHNOLOGY SINGAPORE PTE LTD, Singapore (SG)

( * ) Notice: Subject to any disclaimer, the term of this patent is extended or adjusted under 35 U.S.C. 154(b) by 295 days.

(21) Appl. No.: 14/587,332

(22) Filed: Dec. 31, 2014

(65) Prior Publication Data
US 2015/0198480 A1    Jul. 16, 2015

(30) Foreign Application Priority Data

Jan. 10, 2014  (CN) .......................... 2014 1 0013271

(51) Int. Cl.
| | |
|---|---|
| *G01J 1/04* | (2006.01) |
| *G01J 1/42* | (2006.01) |
| *G01N 21/27* | (2006.01) |

(52) U.S. Cl.
CPC .............. *G01J 1/42* (2013.01); *G01J 1/0437* (2013.01); *G01N 21/274* (2013.01); *G01J 2001/0481* (2013.01); *G01J 2001/4252* (2013.01); *G01N 2201/0622* (2013.01); *G01N 2201/0623* (2013.01); *G09G 2320/045* (2013.01)

(58) Field of Classification Search
None
See application file for complete search history.

(56) References Cited

U.S. PATENT DOCUMENTS

2015/0124253 A1*  5/2015  McCord ................ G01J 1/0407
                                                                     356/326

* cited by examiner

*Primary Examiner* — Kara E Geisel
*Assistant Examiner* — Amanda Merlino
(74) *Attorney, Agent, or Firm* — Ostrolenk Faber LLP

(57) ABSTRACT

Method of generating a correction function for a light-emitting diode (LED) testing process, including: detecting light emitted by a reference LED and reflected from inactive LEDs on a panel within a field of view of a detector; varying a number of the inactive LEDs to derive uncorrected values of an optical parameter as a function of the number of inactive LEDs; detecting light emitted by the reference LED, or by an active LED having identical optical properties, in the absence of any other LEDs, to determine at least one reference value for each optical parameter; and calculating differences between the uncorrected values and each reference value to generate the correction function, the correction function being based on the number of inactive LEDs which are arranged within the field of view of the detector in the light detecting step.

18 Claims, 12 Drawing Sheets

LED TESTING PROCESS AND CORRECTION METHODS THEREFOR

TECHNICAL FIELD

This invention relates to a method of and apparatus for generating a map of correction factors for an LED testing process, and to an LED testing process.

BACKGROUND

The LED manufacturing process typically involves fabrication of arrayed LED units on a printed circuit board (PCB) substrate. The fabrication process includes die attachment, wire bonding, phosphor application and lens attachment, followed by singulation to separate the PCB into the individual LED units. The singulated LED units are tested individually and sorted into bins according to optical and electrical performance before packing.

Optical testing of an LED unit is typically performed by positioning the LED within the input port of an integrating sphere which is coupled to a detector (e.g., to a spectrometer via an optical fiber), measuring optical parameters of the LED unit, and calibrating the LED unit by comparing the measured optical parameters against those of a reference LED on which absolute calibration has previously been performed.

A disadvantage of this post-singulation unit-by-unit testing process is the amount of handling required for each LED, which increases the complexity and cost of the testing, as well as the risk of contamination or damage of the LED.

One previously proposed approach is to directly test the LEDs on the substrate, i.e. prior to singulation, for example using a BTS256-LED tester of Gigahertz-Optik GmbH (Puchheim, Germany). A problem with this approach is that in addition to direct detection of light emitted by the device under test (DUT), an integrating sphere used as part of the testing process can detect indirect light from inactive LEDs adjacent to the DUT. Light from the DUT is reflected from the integrating sphere, is absorbed by phosphors of the adjacent LEDs, and is in turn re-emitted into the detector aperture. In order to alleviate this problem the BTS256-LED, which is a hand-held tester, includes a conical adapter at the input of the integrating sphere, the conical adapter being positionable over the DUT to block out any re-emitted light. However, this device is generally not suitable for high-throughput testing applications as it requires precise manual positioning in both the horizontal and vertical directions in order for the conical adapter to be effective.

There remains a need for a simpler, more cost-effective and higher yield process flow for the testing of LEDs.

SUMMARY

Certain embodiments of the invention relate to a method of generating a correction function for a light-emitting diode (LED) testing process, the method comprising the steps of:

detecting light emitted by a reference LED and reflected from one or more inactive LEDs on a panel within a field of view of a detector, a number of said inactive LEDs within the field of view being varied such that uncorrected values of at least one optical parameter are derivable as a function of the number of inactive LEDs in the field of view;

detecting light emitted by the reference LED, or by an active LED having identical optical properties to the reference LED, in the absence of any other LEDs, to determine at least one reference value for the or each said optical parameter; and calculating differences between the uncorrected values and the or each reference value to generate the correction function, the correction function being based on the number of inactive LEDs which are arranged within the field of view of the detector when the detector detects light emitted by an LED under test.

Other embodiments of the invention relate to an LED testing process performed on a panel of LEDs, the process comprising the steps of:

measuring at least one optical parameter of an LED under test on the panel, light from said LED being emitted within a field of view of an optical detector; determining a number of inactive LEDs on the panel within the field of view;

retrieving or otherwise obtaining a correction factor, said correction factor being derived from a correction function which depends on the number of inactive LEDs which are arranged within the field of view of the detector when the optical detector detects light emitted by the LED under test; and applying the correction factor to the measured optical parameter.

Other embodiments relate to a system for generating a correction function for an LED testing process for a panel of LEDs, the system comprising:

an optical detector having a field of view;

a reference LED having known optical properties;

an actuator for positioning the optical detector to detect light emitted by the reference LED, or by an active LED having identical optical properties to the reference LED, and reflected from one or more inactive LEDs of the panel within the field of view;

a mask for varying a number of said inactive LEDs within the field of view such that uncorrected values of at least one optical parameter of the detected light are derivable as a function of the number of inactive LEDs within the field of view; and at least one processor for calculating differences between the uncorrected values and a reference value, the reference value being determinable by detecting light emitted by the reference LED or the active LED in the absence of any other LEDs to generate the correction function, the correction function being based on the number of inactive LEDs which are arranged within the field of view when the optical detector detects light emitted by an LED under test.

Further embodiments relate to a system for generating a correction function for an LED testing process for a panel of LEDs, the system comprising:

an optical detector having a reflective internal surface and an input port defining a field of view, the optical detector being configured to measure at least one optical parameter of light detected by the optical detector;

a reference LED having known optical properties and being positionable to illuminate the internal surface of the optical detector;

a diffusely-reflecting reference surface over which the input port is positionable to detect reflected light from the reference surface; and an actuator for positioning the input port over the panel at a plurality of locations to thereby vary a number of LEDs within the field of view, to illuminate said LEDs with light reflected from the internal surface of the detector, and to detect light reflected from said LEDs;

wherein:

the input port is positionable over the diffusely-reflecting reference surface to measure the at least one optical parameter and to thereby obtain a reference value for the at least one optical parameter; and the input port is positionable over the plurality of locations to obtain a plurality of uncorrected values for the at least one optical parameter.

Yet further embodiments relate to a method of generating a map of correction factors for an LED testing process, the method comprising the steps of:

detecting light emitted by a reference LED and reflected from one or more inactive LEDs which neighbor a location on a panel of LEDs, the location being varied such that uncorrected values of at least one optical parameter are derivable as a function of location;

detecting light emitted by the reference LED, or by an active LED having identical optical properties to the reference LED, in the absence of any other LEDs, to determine at least one reference value for the or each said optical parameter; and calculating differences between the uncorrected values and the or each reference value to generate the map of correction factors, the map of correction factors being based on the number of inactive LEDs which are arranged within the field of view of the detector when the detector detects light emitted by the LED under test.

BRIEF DESCRIPTION OF THE DRAWINGS

Embodiments of the invention will now be described, by way of non-limiting example only, with reference to the accompanying drawings in which.

DETAILED DESCRIPTION

Embodiments of the present invention provide a method of directly testing an array of LED units on a substrate, rather than first requiring singulation. A map of testing results, containing measured optical and electrical characteristics as a function of position within the array, can be generated and used to bin the LEDs prior to singulation and packing. The method has higher throughput than previously known methods, as fewer unit handling processes are needed. By reducing the amount of handling, the risk of damage or contamination is also reduced.

Figure 1:
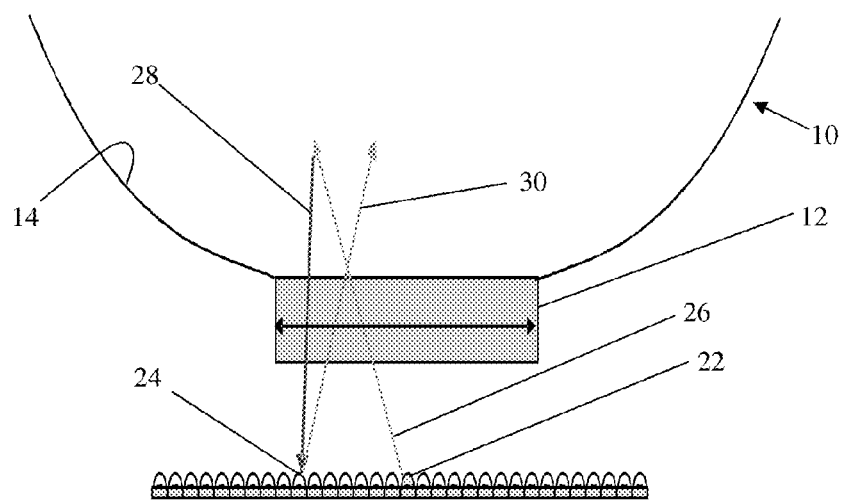
FIG. 1 schematically depicts the spatial relationship between an optical detector and an LED panel during an optical testing process.

The present inventors have realized, for the first time, that LEDs can be tested on-panel in a high throughput fashion, by appropriately correcting for light which is re-emitted from phosphors of those inactive LEDs which neighbor the device under test. The re-emission problem is illustrated in FIG. 1, in which detector apparatus including an integrating sphere 10 having an input port 12 is positioned over an LED 22 (the device under test) which is active and emitting light into the input port 12 (for example, in the direction indicated by arrow 26, though it will be appreciated that LEDs will typically have an emission region, for example a cone). The integrating sphere 10 is coupled to a spectrometer via an optical fiber bundle (not shown). The fiber bundle captures light received directly from LED 22 and reflected (possibly multiple times) from diffusely reflective internal surface 14 of integrating sphere 10.

Due to the diffuse reflection from surface 14, some of the light from LED 22 will be reflected back out of the input port, for example in the direction indicated by arrow 28. Light reflected in direction 28 can be partly absorbed by the phosphor coating of LED 24, and re-emitted into the input port 12 (e.g. in direction 30). Accordingly, re-emitted light from inactive LEDs neighboring the device under test (DUT) can provide a spurious contribution to measurement of optical parameters of the DUT.

The present inventors have found that the above described re-emission effect increases with the number of neighboring inactive LEDs (also called background LEDs herein) within the field of view of the integrating sphere. The number of neighboring LED units of a DUT varies with the DUT location on the panel. For example, if the DUT is at the center of the panel, the adjacent units are in all 4 quadrants of the field of view; if the DUT is at the corner of the panel, the adjacent units only cover 1 quadrant.

Accordingly, embodiments of the present invention aim to determine a correction map or correction function comprising a set of correction factors, one for each LED on a panel to be tested, which offset the re-emission effect of the corresponding location of the DUT on the panel. The correction factors are determined once, prior to testing of any panels being carried out, and can then be used in testing of multiple panels during a production run in an LED panel testing apparatus.

Figure 2:
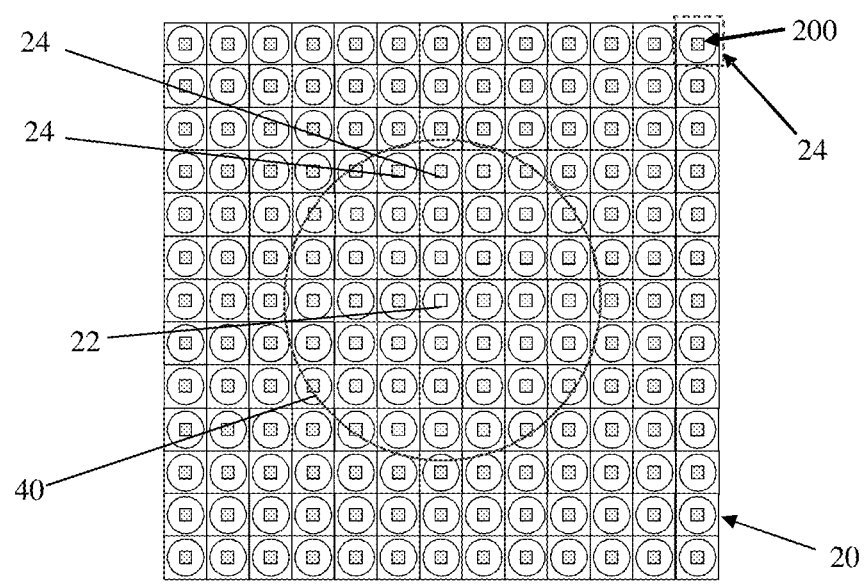
FIG. 2 is a top elevation view of the LED panel.

As shown in FIG. 2, an exemplary LED panel 20 includes a plurality of LED units 22, 24 arranged in a matrix. The projected field of view of the input port 12 of integrating sphere 10, when centered on DUT 22, is depicted by circle 40. Multiple LEDs 24 (only two of which are labeled, for clarity) surround the DUT 22 and lie at least partially within circle 40. Each LED unit 22 or 24 comprises a chip 200 which is to be packaged in conventional fashion.

In the illustrated example, each LED unit 22 or 24 is 3.5 mm wide and the input port 12 has an opening which is 24.5 mm in diameter, such that 45 LEDs, including the DUT 22 and 44 neighboring inactive (background) LEDs, lie at least partially within the circle 40. As the detector aperture and thus the field of view 40 is moved to different positions over panel 20, in particular as the field of view 40 approaches the edges or corners of the panel, the number of background (inactive) LEDs within the field of view 40 will decrease. This can be exploited in order to derive a correction factor as a function of the number of background LEDs (or equivalently, the area of the field of view which contains background LEDs) as will later be described in detail.

Advantageously, knowledge of the layout of a particular LED panel can be used to determine a finite number of patterns or possibilities (substantially less than the number of possible LED positions) for the number of background LEDs which will be within the field of view for various DUT locations on the panel.

For example, if the panel has a regular array of LEDs, then each of the four corner LEDs will have the same number of background LEDs, such that a correction factor need only be determined for one of the four corners. Similarly, for DUTs near the center of the panel and away from the edges, the number of background LEDs will be constant, such that the correction factor can be determined once at the center of the panel and used for each LED which is near enough to the center to have the same number of background LEDs.

An exemplary method 400 of generating correction factors for an LED panel will now be described with reference to the flow chart of FIG. 3 and to the schematic of FIG. 4.

In certain embodiments, a method 400 involves positioning (block 410) a panel 500 of LEDs within a field of view 520 of an integrating sphere (with associated spectrometer, etc.). The panel 500 comprises at least one standard LED 510 having known electrical and optical properties determined by independent testing methods such as those specified in CIE 127:2007. The standard LED 510 is used as a reference LED for correction factor generation. The remaining LEDs (omitted for clarity) are arranged in rows and columns with the reference LED 510 lying in one of the rows/columns. The remaining LEDs may also be standard LEDs, or may be production LEDs to be delivered to a customer following testing, or a combination of the two.

The input port of the integrating sphere is positioned with its center over the reference LED 510 (block 420). Movement of the integrating sphere may be effected by any suitable means, for example using one or more actuators coupled to a controller which is configured to drive the actuators in accordance with a predetermined schedule of movements and/or in accordance with user input. The controller may be operatively coupled to, or may be, a standard computer system such as a 32-bit or 64-bit Intel Architecture-based computer system. The computer system may include standard computer components, including random access memory (RAM), at least one processor, and external interfaces, all interconnected by a bus. The external interfaces may include a network interface connector (NIC) which connects the system to a communications network. The system may also include a number of standard software modules, including an operating system such as Linux or Microsoft Windows, and may include one or more modules for driving the one or more actuators and/or other physical components.

Figure 4:
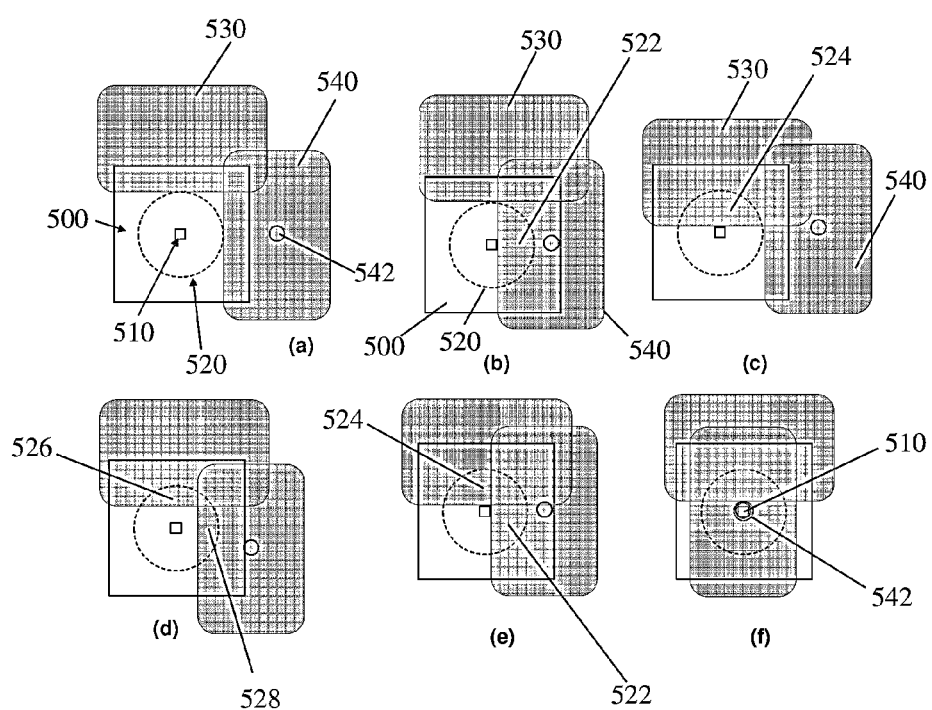
FIG. 4 shows a series of mask positions for the process of FIG. 3.

As shown in FIG. 4, an x-mask 540 and a y-mask 530 may be moved to various positions so as to mask variable portions of the field of view 520. Non-volatile memory of the controller and/or the computer system may have stored thereon data relating to the positions to which the masks 530, 540 should be moved, and program instructions for driving mask actuators for effecting movement to the various positions.

At block 430 of process 400, the controller selects the next mask position, for example a position as shown in FIG. 4(a) in which the perimeter of the field of view 520 is aligned with respective edges of the two masks 530, 540, such that none of the field of view is masked out. At block 440, the mask(s) are actuated (if required) and positioned over neighbouring LEDs (if any) of the reference LED 510. At each selected mask position, the reference LED output is measured by the integrating sphere (block 450). If there are still further mask positions to be iterated through, the process loops back from block 460 to block 430, the next mask position is selected, and the masking/measurement sequence 440, 450 is repeated.

Different mask positions may be selected in order to mask out the field of view such that a certain proportion (area) of the field of view remains unmasked. Alternatively, specific rows or columns of LEDs may be masked out. It will be appreciated, though, that masking of certain LEDs within the field of view 520 may be closely equivalent to masking of other LEDs. For example, in FIG. 4(b), a portion 522 is masked out by x-mask 520. Portion 522 covers approximately half (the right-hand half) of the field of view 520, noting that it is not possible to mask out exactly half without also partially masking the reference LED 510. Masking out the portion of the field of view 520 to the left of reference LED 510 would be equivalent to the configuration shown in FIG. 4(b) due to the symmetry of the field of view. Accordingly, a measurement need only be made using the configuration of FIG. 4(b).

It will also be appreciated that the mask positions shown in FIGS. 4(a) to 4(e) allow simulation of the re-emission effect experienced at different locations on the panel 510, without needing to re-position the integrating sphere at different locations and without needing to modify the aperture of the integrating sphere. The mask positions correspond to:

Center (and near the center) of the panel (FIG. 4(a));
Right-hand edge of the panel (FIG. 4(b));
Top edge of the panel (FIG. 4(c));
Top right corner, inset by e.g. one row and one column (FIG. 4(d)); and
Top right corner (FIG. 4(e)).

If all mask positions have been exhausted, the process proceeds to block 470, where the entire field of view 520 is masked out except in the region of reference LED 510. This is achieved by virtue of aperture 542 of x-mask 540, which is sized and shaped to allow unimpeded emission from reference LED 510 whilst blocking all of its neighbors, as shown in FIG. 4(f). A measurement of reference LED 510 is then taken. As this measurement should be free of any re-emission effect, it is used as a reference measurement against which the measurements in the other mask positions are to be compared to compute the correction factors (block 480).

In alternative embodiments, the reference measurement can be obtained by measurement of a single active LED (not shown), i.e., which does not have any neighbouring inactive LEDs. The active LED should have the same optical parameters as the reference LED 510 in order to be able to be used for comparison purposes in calculating the correction factors. The active LED may be located in a dedicated region of the panel 500 such that no other LEDs are in the dedicated region, or may be a single off-panel LED which can be activated and measured in the absence of any other LEDs in order to obtain the reference measurement.

The correction factors computed at block 480 are calculated for at least one optical parameter, and in certain embodiments for more than one. In one exemplary embodiment, each measurement derives optical parameters from the spectral power distribution (as measured by the spectrometer coupled to the integrating sphere), for example two color coordinates (such as CIE x and CIE y) and a luminance or flux parameter. Accordingly, each correction factor represents the difference between a parameter (such as CIE x) measured under a particular masking configuration (e.g. as in FIG. 4(a) to FIG. 4(e)) and the parameter measured with no re-emission effect, i.e. the reference value obtained via the measurement depicted in FIG. 4(f). If three optical parameters are measured then the process 400 generates a triplet of correction factors for each masking configuration, i.e. a vector-valued correction function which depends on the number of (unmasked) background LEDs.

The correction function or correction map, comprising the correction factors calculated by process 400, can be stored and used as input to an LED testing process carried out on a panel of LEDs. The LED testing process measures optical parameters of each LED on a panel of LEDs. Then a correction is applied to the measured values, using the correction function or correction map, based on the locations of the respective tested LEDs on the panel.

In one example, the result of process 400 is a correction map in which $\Delta_{ij}$ is the correction factor at location (i, j). If the test panel has an identical layout to the panel used to derive the correction map, then the corrected parameter value is given by $x_{ij}^1 = x_{ij} - \Delta_{ij}$, where $x_{ij}$ is the originally measured value for the LED at location (i, j) within the array. In another example, the result of process 400 is a correction function $\Delta(\#\text{background LEDs})$, i.e. the correction factor is a function of the number of LEDs within the field of view. If the layout of the test panel is not identical to the layout of the panel used to derive the correction function, then for each LED location on the test panel, a number of neighboring background LEDs can be determined prior to the testing process, and the number passed to $\Delta(\#\text{background LEDs})$ to determine the appropriate correction factor. A combination of these two approaches is also possible.

Figure 3:
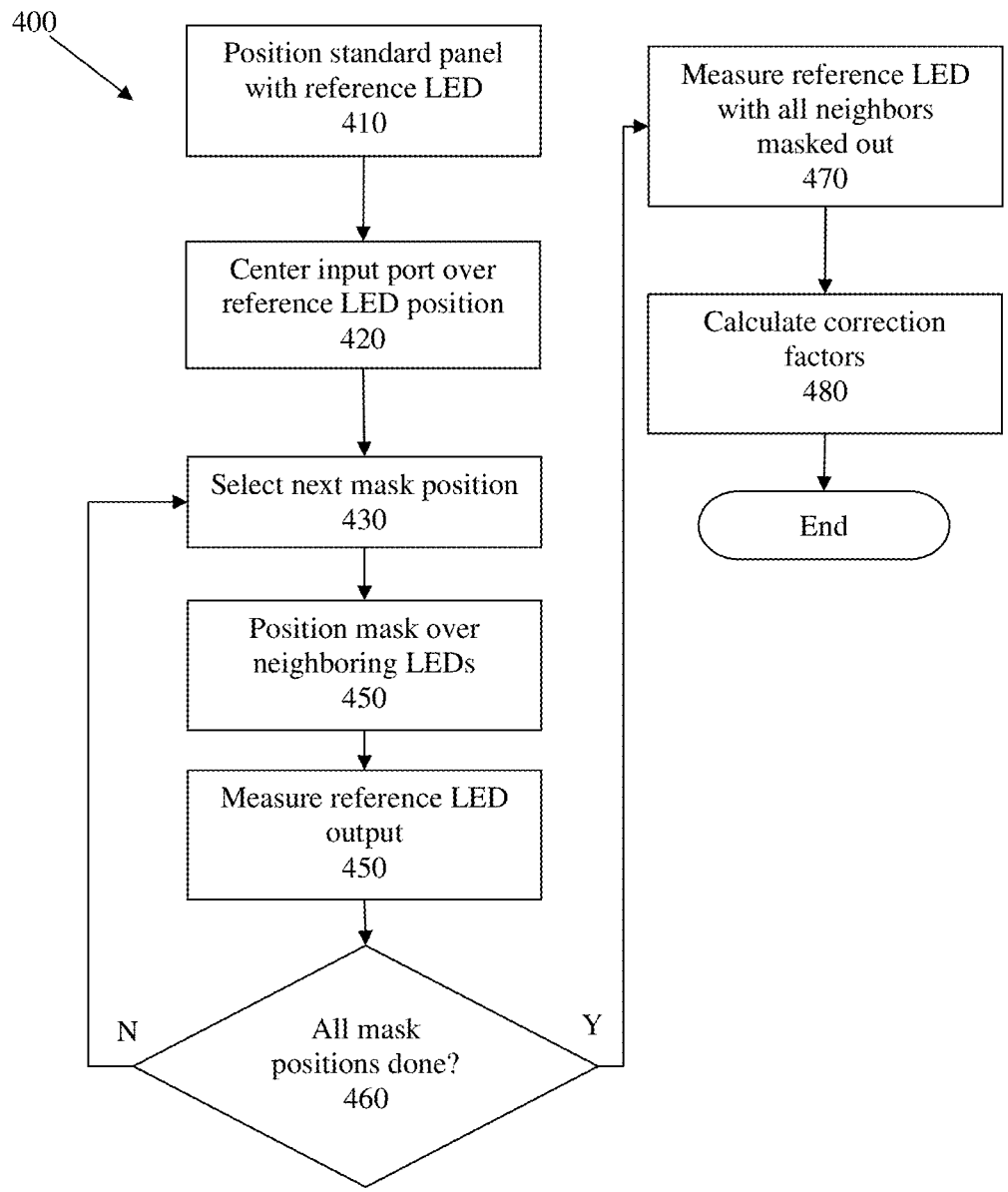
FIG. 3 is a flow chart of a method of generating a correction function according to an embodiment of the invention.
Figure 5:
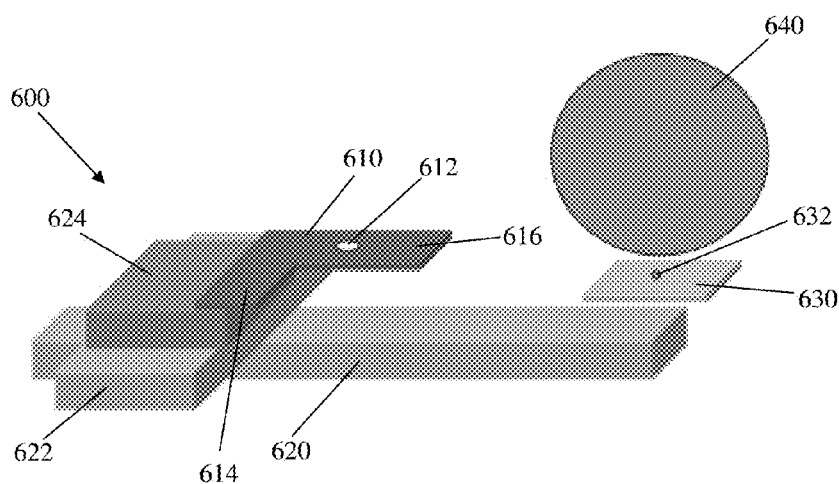
FIGS. 5 to 7 are perspective views of a system for generating a correction function according to an embodiment.
Figure 6:
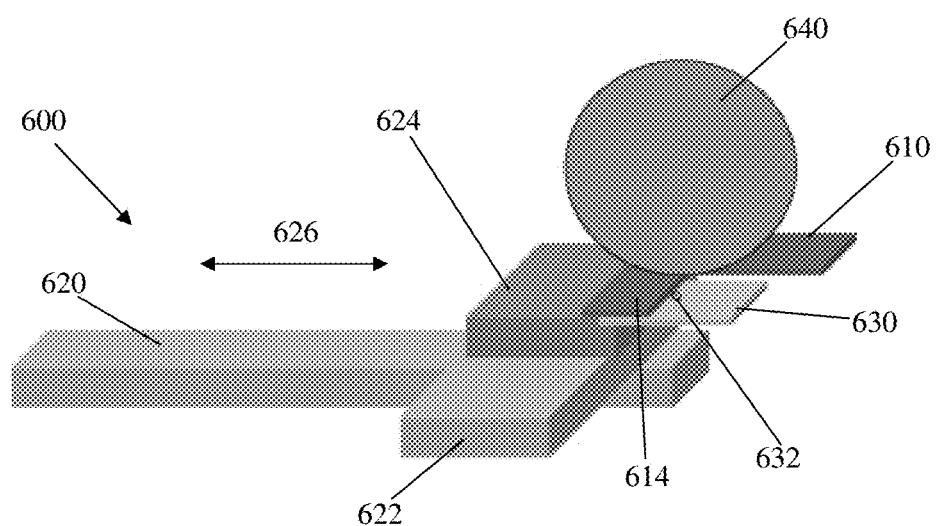
Figure 7:
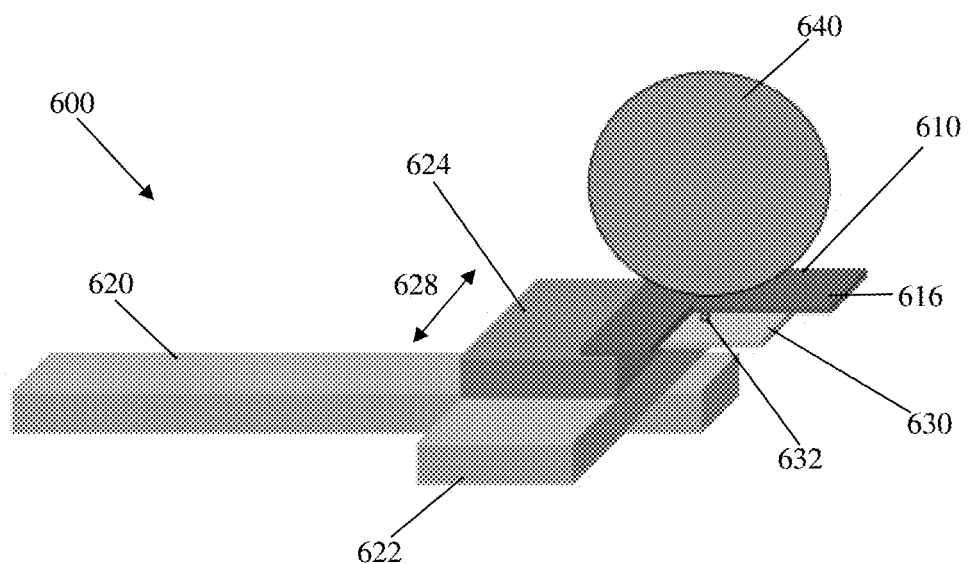

An alternative system 600 for implementing the mask-based process 400 shown in FIG. 3 and FIG. 4 is shown in FIGS. 5 to 7. The flow of process 400 proceeds substantially as described above, but uses an alternative physical mechanism. The system 600 comprises an L-shaped mask component 610 having an aperture 612 mounted to an xy-translation stage 620 having a first movable member 622 and a second movable member 624. The first movable member 622 is configured for movement along translation stage 620 along a direction 626. The second movable member 624 is configured for movement along the first movable member 622 along a direction 628 which is orthogonal to direction 626. The first 622 and second 624 movable members together allow the L-shaped mask component to be positioned relative to LED panel 630 on which reference LED 632 and a plurality of additional LEDs (not shown) are disposed. Integrating sphere 640 is positioned above panel 630 such that its input port is centered over reference LED 632.

Two exemplary configurations of the system 600 are shown. In FIG. 6, the first movable member 622 is moved along direction 626 until a first arm 614 (equivalent to y-mask 530 of FIG. 4) of the mask component 610 covers approximately half of the field of view under integrating sphere 640, similarly to the masking configuration shown in FIG. 4(c). In FIG. 7 the first movable member 622 stays fixed and the second movable member 624 is moved along direction 628 so that second arm 616 (equivalent to x-mask 540 of FIG. 4) covers an additional portion of the field of view in similar fashion to the arrangement of FIG. 4(e). The fraction of the field of view which is covered can be varied as desired by appropriate movement of members 622, 624. By virtue of the aperture 612 in second arm 616, the entire field of view apart from in the region of reference LED 632 can be covered, in order to obtain a reference measurement as discussed above. In alternative embodiments, in order to obtain a reference measurement, the output of an active LED having no neighbouring LEDs, but having the same optical parameters as the reference LED 632, can be measured.

Figure 8:
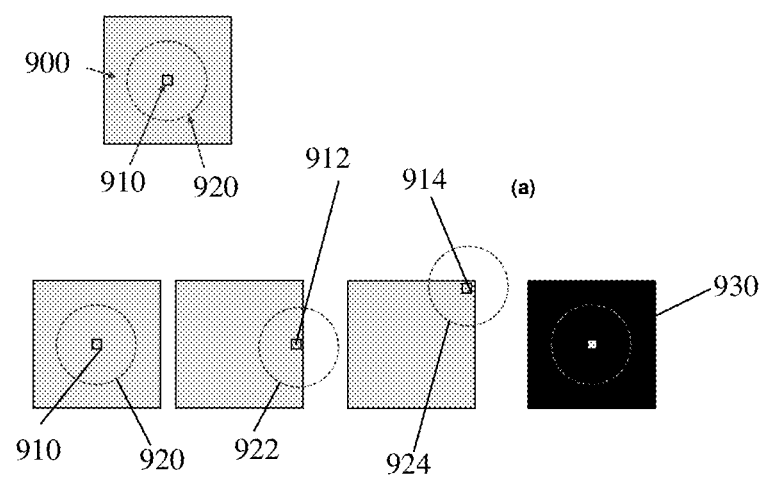
FIG. 8 schematically depicts an LED panel in use during a method according to another embodiment.

Turning now to FIG. 8, there is schematically depicted a further alternative method of deriving correction factors for an LED testing process. In FIG. 8, a panel 900 of LEDs comprises a plurality of reference LEDs 910, 912, 914 at different positions within an array of LEDs on the panel. Only the reference LEDs are shown for reasons of clarity.

Each reference LED 910, 912, 914 is a standard LED with known optical parameters. For each different reference LED position, a different number of neighboring LEDs is present. For example, reference LED 910 is at the center of array 900 and has the maximum number of neighbors given a fixed field of view 920, analogously to the situation shown in FIG. 4(a). On the other hand, reference LED 912 is at an edge and has approximately half the number of neighbors as LED 910, analogously to the situation shown in FIG. 4(b). Reference LED 914 is a corner LED, which has approximately a quarter the number of neighbors as LED 910.

Although only three reference LED positions are specifically shown in FIG. 8, it will be appreciated that in order to derive a correction factor for each unique pattern of neighboring LEDs, a reference LED should be placed in at least one location which corresponds to that pattern. In some embodiments, more than one reference LED per unique pattern may be used, and the average (for example) of the resulting correction factors may then be computed.

The output of each reference LED 910, 912 or 914 is measured as described above. Each measurement is then compared to a reference measurement which is taken with the entire field of view masked out by mask 930, except in the region of reference LED 910, 912 or 914. A map of correction factors can then be generated by computing the differences between the masked and unmasked measurements, and assigning a correction factor to each LED location on the panel 900 according to the number of neighboring LEDs at respective locations. In alternative embodiments, the reference measurements can be obtained without a mask, by using active LEDs (not shown) which do not have any neighbouring LEDs and so which do not result in measurements tainted by the re-emission effect. Each active LED has identical optical parameters to one of the reference LEDs 910, 912 or 914. Reference measurements for deriving the correction factors can then be obtained by measuring the respective active LEDs.

Figure 9A:
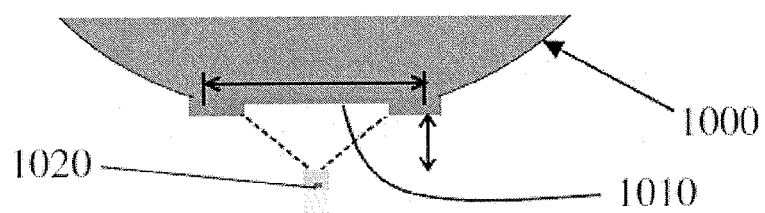
FIG. 9(a) and FIG. 9(b) illustrate an optical detector and LED panel in use during a method according to a further embodiment.
Figure 9B:
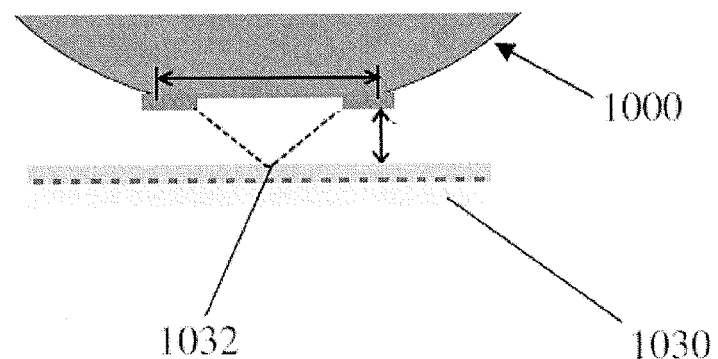
Figure 10:
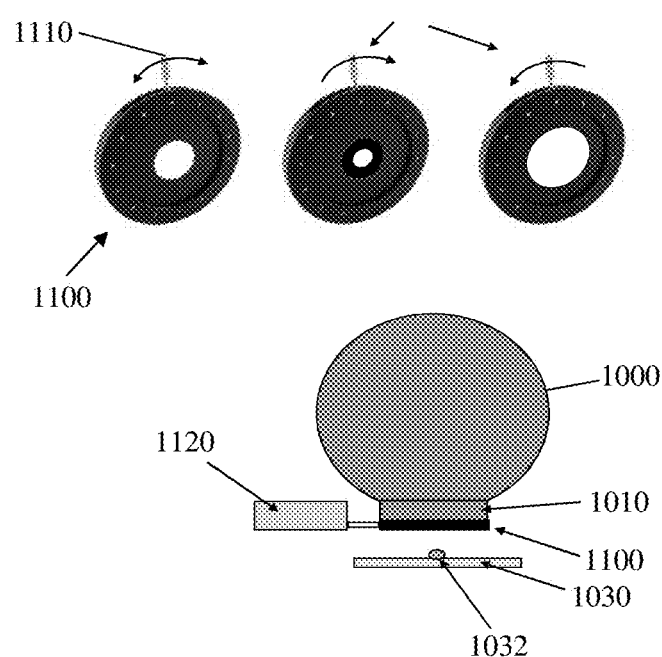
FIG. 10 shows the optical detector of FIG. 9 in more detail.

FIG. 9 and FIG. 10 depict apparatus for use in yet further embodiments of a method for generating a correction function or a correction map. In FIG. 9(a), an integrating sphere 1000 has within its field of view a single active LED 1020 having known optical properties. Since the active LED 1020 has no neighbors, the output should be free of any re-emission effect, and the measured optical parameters can be used as reference values. In FIG. 9(b), a reference LED 1032 having identical optical properties to active LED 1020 is located within a panel 1030 of LEDs.

Because reference LED 1032 has neighboring LEDs within the field of view of integrating sphere 1000, on-panel measurements of reference LED 1032 will include a contribution from re-emission from phosphors of the inactive neighboring LEDs, as explained previously.

In order to estimate the re-emission effect as a function of the number of neighboring LEDs, integrating sphere 1000 can be provided with a variable aperture such that the field of view, and hence the number of neighbors of reference LED 1032, can be varied. In certain embodiments this is achieved by coupling a diaphragm 1100 to the input port 1010 of integrating sphere 1000. The aperture of diaphragm 1100 can be varied as shown in FIG. 10, either manually or automatically (e.g., using a servomechanism 1120), by adjusting handle 1110 to either open or close the diaphragm 1100. A measurement of the optical parameters of reference LED 1032 is taken for each aperture size, and the differences between the measured parameters and the reference values are computed to generate correction factors as a function of aperture size (or equivalently, as a function of the number of neighboring LEDs).

Figure 11:
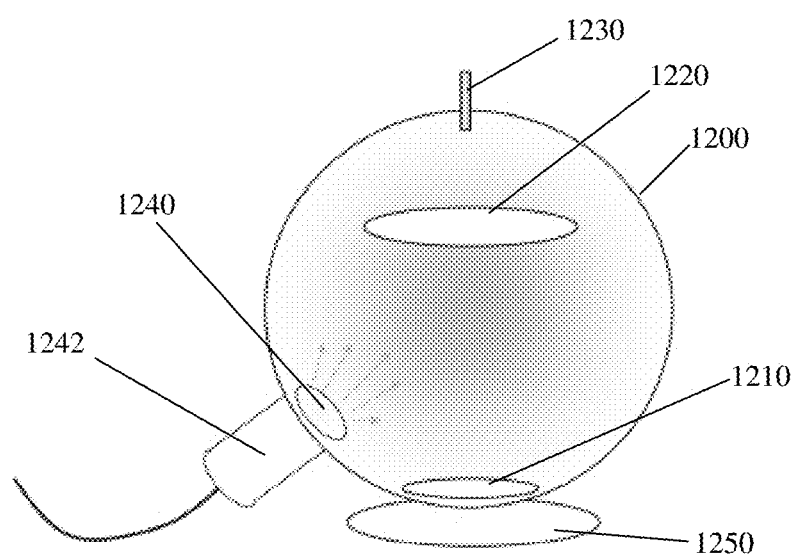
FIG. 11 and FIG. 12 show apparatus for implementing a method according to a yet further embodiment of the invention.
Figure 12:
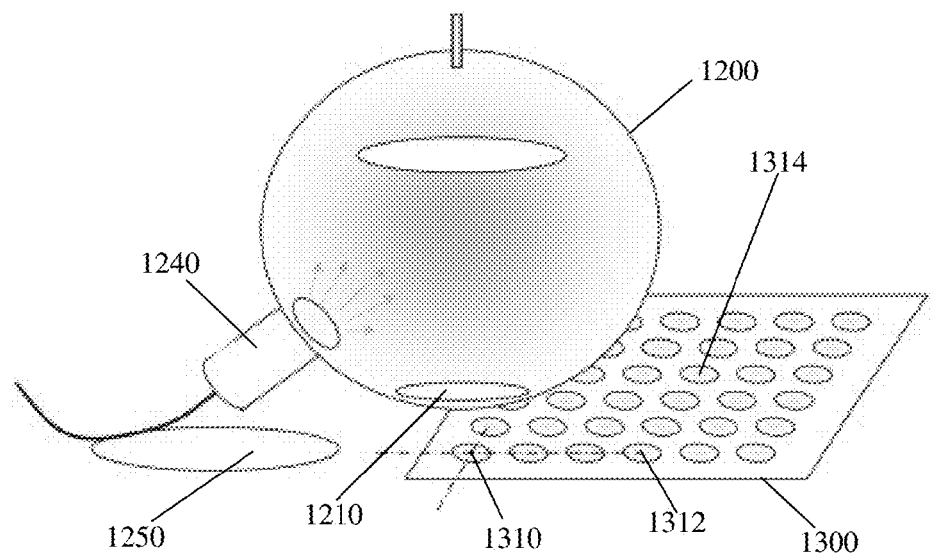

Turning now to FIG. 11 and FIG. 12, even further alternative embodiments of a method of generating correction factors are depicted.

In FIG. 11, an integrating sphere 1200 having an input port 1210, baffle 1220 and fiber bundle 1230 (for optically coupling the sphere 1200 to a spectrometer, not shown) is positioned with input port 1210 above a white, diffusely reflecting reference surface 1250. The integrating sphere has a second input port 1240 to accommodate an LED holder 1242 which houses a reference LED having known optical properties. The reference LED illuminates the internal surface of integrating sphere 1200, which detects light reflected from the internal surface as well as light reflected from the reference surface 1250. A measurement recorded by the spectrometer coupled to integrating sphere 1200 is used to calculate reference values for optical parameters of the reference LED.

Next, as depicted in FIG. 12, the integrating sphere 1200 is moved away from reference surface 1250 and positioned with input port 1210 centered over an LED 1310 in a panel 1300 of LEDs. All LEDs of panel 1300 are inactive. The reference LED is again used to illuminate the internal surface of integrating sphere 1200 but this time, LEDs which are within the field of view of sphere 1200 will produce a re-emission effect due to absorption of light from the reference LED which is reflected onto the array 1300. The degree of the re-emission effect depends on the number of LEDs, or equivalently the re-emitting area, within the field of view. This in turn depends on the respective locations of the LEDs. For example, corner LED 1310 has fewer neighbors than edge LED 1312 or a more centrally located LED 1314. Accordingly, in order to generate a correction map, the position of integrating sphere 1200 can be varied so as to cover all possible unique patterns of neighboring LEDs. The measured value of an optical parameter for each unique pattern can be compared to the reference value obtained in the absence of any LEDs (i.e., with the sphere 1200 positioned over the reference surface 1250) in order to obtain a correction factor for each unique pattern and thus to generate the correction map.

Although particular embodiments of the invention have been described in detail, many modifications and variations are possible within the scope of the invention, as will be clear to a skilled reader.

The invention claimed is:

1. A method of generating a correction function for a light-emitting diode (LED) testing process, the method comprising the steps of:
    detecting light emitted by a reference LED and reflected from one or more inactive LEDs on a panel within a field of view of a detector, a number of said inactive LEDs within the field of view being varied such that uncorrected values of at least one optical parameter are derivable as a function of the number of inactive LEDs in the field of view;
    detecting light emitted by the reference LED, or by an active LED having identical optical properties to the reference LED, in the absence of any other LEDs, to determine at least one reference value for said at least one optical parameter; and
    calculating differences between the uncorrected values and said at least one reference value to generate a correction function, the correction function being based on the number of inactive LEDs which are arranged within the field of view of the detector when the detector detects light emitted by an LED under test.

2. The method according to claim 1, wherein the number of inactive LEDs is varied by varying an area of the panel which is within the field of view.

3. The method according to claim 2, wherein the number of inactive LEDs is varied by selectively masking either the field of view or the panel, or both.

4. The method according to claim 2, wherein the number of inactive LEDs is varied by varying the location of the reference LED on the panel.

5. The method according to claim 4, wherein the position of the active LED is selected from the group consisting of: an interior region where the area of a sampled region is a maximum; at least one corner region; and at least one edge region.

6. The method according to claim 3, comprising varying an aperture of an input port of the detector.

7. The method according to claim 1, wherein said reference LED is located on a standard panel of reference LEDs, said standard panel having the same LED layout as said panel.

8. The method according to claim 1, comprising the steps of:
    illuminating the interior surface of an integrating sphere with the reference LED with an input port of the integrating sphere positioned over a diffusely reflecting surface, to obtain the reference value;
    positioning the input port at a plurality of locations, the field of view at each location having a different number of inactive LEDs located therein;
    measuring the at least one optical parameter at the plurality of locations to obtain the uncorrected values for the at least one optical parameter; and
    calculating differences between the uncorrected values and said at least one reference value.

9. The method according to claim 1, wherein said at least one optical parameter is selected from the group consisting of: a chromaticity coordinate, correlated color temperature (CCT), color rendering index (CRI), radiant flux and luminous flux.

10. An LED testing process performed on a panel of LEDs, the process comprising the steps of:
    measuring at least one optical parameter of an LED under test on the panel, light from said LED being emitted within a field of view of an optical detector;
    determining a number of inactive LEDs on the panel within the field of view;
    obtaining a correction factor, said correction factor being derived from a correction function which depends on the number of inactive LEDs which are arranged within the field of view of the detector when the optical detector detects light emitted by the LED under test; and
    applying the correction factor to the measured optical parameter.

11. The process according to claim 10, further comprising generating the correction function.

12. The process according to claim 11, wherein said generating comprises:
    detecting light emitted by a reference LED and reflected from one or more inactive LEDs within a field of view, a number of said inactive LEDs being varied such that uncorrected values of at least one optical parameter are derivable as a function of the number of inactive LEDs within the field of view;

detecting light emitted by the reference LED, or by an active LED having identical optical properties to the reference LED, in the absence of any other LEDs, to determine at least one reference value for said at least one optical parameter; and calculating differences between the uncorrected values and said at least one reference value to generate the correction function, the correction function being based on the number of inactive LEDs which are arranged within the field of view when the optical detector detects light emitted by an LED under test.

13. A system for generating a correction function for an LED testing process for a panel of LEDs, the system comprising:

an optical detector having a field of view;

a reference LED having known optical properties;

an actuator for positioning the optical detector to detect light emitted by the reference LED, or by an active LED having identical optical properties to the reference LED, and reflected from one or more inactive LEDs of the panel within the field of view;

a mask for varying a number of said inactive LEDs within the field of view such that uncorrected values of at least one optical parameter of the detected light are derivable as a function of the number of inactive LEDs within the field of view; and at least one processor for calculating differences between the uncorrected values and a reference value, the reference value being determinable by detecting light emitted by the reference LED or the active LED in the absence of any other LEDs to generate a correction function, the correction function being based on the number of inactive LEDs which are arranged within the field of view when the optical detector detects light emitted by an LED under test.

14. The system according to claim 13, wherein said mask is movable to mask a variable portion of the panel within the field of view, thereby to vary the number of inactive LEDs within the field of view.

15. The system according to claim 14, wherein said mask is operatively coupled to an XY translation stage.

16. The system according to claim 13, wherein said mask comprises a diaphragm coupled to an input port of the detector.

17. A system for generating a correction function for an LED testing process for a panel of LEDs, the system comprising:

an optical detector having a reflective internal surface and an input port defining a field of view, the optical detector being configured to measure at least one optical parameter of light detected by the optical detector;

a reference LED having known optical properties and being positionable to illuminate the internal surface of the optical detector;

a diffusely-reflecting reference surface over which the input port is positionable to detect reflected light from the reference surface; and an actuator for positioning the input port over the panel at a plurality of locations to thereby vary a number of LEDs within the field of view, to illuminate said LEDs with light reflected from the internal surface of the detector, and to detect light reflected from said LEDs;

wherein:

the input port is positionable over the diffusely-reflecting reference surface to measure the at least one optical parameter and to thereby obtain a reference value for the at least one optical parameter; and the input port is positionable over the plurality of locations to obtain a plurality of uncorrected values for the at least one optical parameter.

18. A method of generating a map of correction factors for an LED testing process, the method comprising the steps of:

detecting light emitted by a reference LED and reflected from one or more inactive LEDs which neighbor a location on a panel of LEDs, the location being varied such that uncorrected values of at least one optical parameter are derivable as a function of location;

detecting light emitted by the reference LED, or by an active LED having identical optical properties to the reference LED, in the absence of any other LEDs, to determine at least one reference value for said at least one optical parameter; and calculating differences between the uncorrected values and said at least one reference value to generate the map of correction factors, the map of correction factors being based on the number of inactive LEDs which are arranged within the field of view of the detector when the detector detects light emitted by the LED under test.

* * * * *